US006359989B2

(12) United States Patent
Hickman et al.

(10) Patent No.: US 6,359,989 B2
(45) Date of Patent: Mar. 19, 2002

(54) ACOUSTIC FILTER APPARATUS FOR AN ELECTRONIC DEVICE

(75) Inventors: Scott N. Hickman, Corvallis; John R. Sterner, Albany, both of OR (US)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/167,624

(22) Filed: Oct. 6, 1998

(51) Int. Cl.[7] .................................................. A61F 11/06
(52) U.S. Cl. ..................... 381/71.5; 381/71.3; 381/71.1
(58) Field of Search ............................... 381/71.3, 71.5, 381/71.1, 94.1; 181/198, 207, 202

(56) References Cited

U.S. PATENT DOCUMENTS 5,502,869 A * 4/1996 Smith et al. ............... 381/71.3

OTHER PUBLICATIONS

Beranek, Leo L.; Acoustics, 1993, pp. 67, 68, 133, 136–137, 143, 353–360.

* cited by examiner

*Primary Examiner*—Minsun Oh Harvey

(57) ABSTRACT

An apparatus for reducing noise emitted by an electronic or other device and such devices incorporating the noise reducing apparatus. A mechanism for acoustically filtering undesired noise from an electronic device, particularly noise generated by a cooling mechanism is disclosed. In a preferred embodiment, noise is filtered at least in part with an appropriately dimensioned compressible air space. The noise reducing or filtering mechanism may be utilized with portable and non-portable computers, stereos, entertainment equipment and other devices.

13 Claims, 2 Drawing Sheets

ACOUSTIC FILTER APPARATUS FOR AN ELECTRONIC DEVICE

FIELD OF THE INVENTION

The present invention relates to noise suppression or filtering in an electronic device. While applicable to all electronic devices, the present invention is particularly applicable to portable electronic devices because of their size and physical feature constraints.

BACKGROUND OF THE INVENTION

There has been a continual effort to develop new features and improve existing features performed by electronic devices. The features may include, but are not limited to, communication, document production, information storage and retrieval, navigation, entertainment, etc. This effort has been at least in part promoted by advances in integrated circuit technology that have produced more powerful processing circuitry. As the complexity of integrated circuits increased, however, the need to adequately cool these devices also increased. While various approaches have been brought forth, cooling by electric fan is the most common technique for integrated circuit and overall electronic device cooling.

While beneficial as a cooling mechanism, conventional fans are disadvantageous in that they produce audible noise at frequencies that are unpleasant to the human ear. While a problem in desk top environments, such as in a desk top computer, the problem is more acute in portable electronic devices. One reason for this is that components are more tightly coupled in a portable device leading to thermal build up. In addition, due to their limited size and weight it is generally more difficult to design new features (such as noise suppression) into a portable device.

Hence a need exists for suppressing or reducing noise generated by the cooling mechanism of an electronic device.

SUMMARY OF THE INVENTION

Accordingly, it is an object of the present invention to reduce or filter noise generated by a cooling mechanism of an electronic device.

It is another object of the present invention to reduce or filter noise generated by a cooling mechanism of a portable electronic device.

It is another object of the present invention to provide noise reduction that filters out frequencies that are unpleasant to a human ear.

It is also an object of the present invention to create a mechanism or structure in a cooling mechanism output path that absorbs, compresses or otherwise attenuates sound waves of particular frequencies.

These and related objects of the present invention are achieved by use of a acoustic filter apparatus of an electronic device as described herein.

The attainment of the foregoing and related advantages and features of the invention should be more readily apparent to those skilled in the art, after review of the following more detailed description of the invention taken together with the drawings.

DETAILED DESCRIPTION

Figure 1:
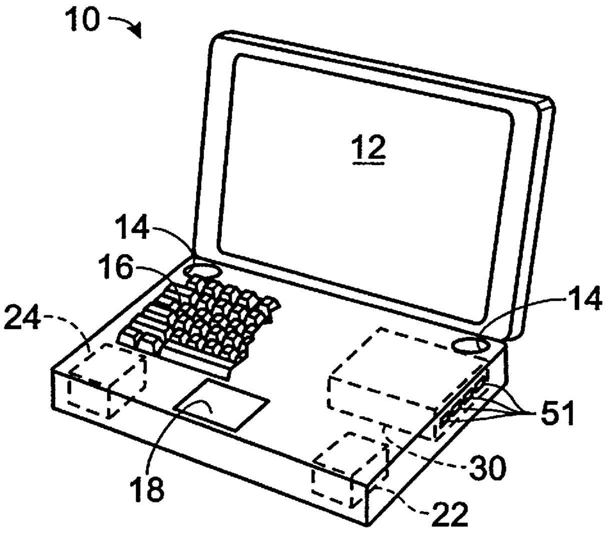
FIG. 1 is a perspective view of an electronic device having noise suppression in accordance with the present invention.

Referring to FIG. 1, a perspective view of an electronic device having noise suppression in accordance with the present invention is shown. As illustrated in FIG. 1, the electronic device is a portable computer, such as a notebook computer. This embodiment, however, is a representative embodiment and it should be recognized that the present invention is applicable to any electronic device, including audio receivers, amplifier units, etc., in which it is desired to reduce noise.

Electronic device 10 preferably includes a display 12 and may include speakers 14 or other output devices including, but not limited to, an information panel or the like (with or without light emitting diodes, etc.) for an audio receiver or related devices. Electronic device 10 also preferably includes a keypad 16 and a pointing mechanism 18 (e.g., a touch pad, track ball, mouse, joy stick, etc., for a computer implementation) or other input devices. Processing circuitry 22 and memory 24 are shown in phantom lines as is cooling system 30 which is discussed in more detailed below. The exhaust of cooling mechanism 30 exits the electronic device through exhaust openings 51.

Figure 2:
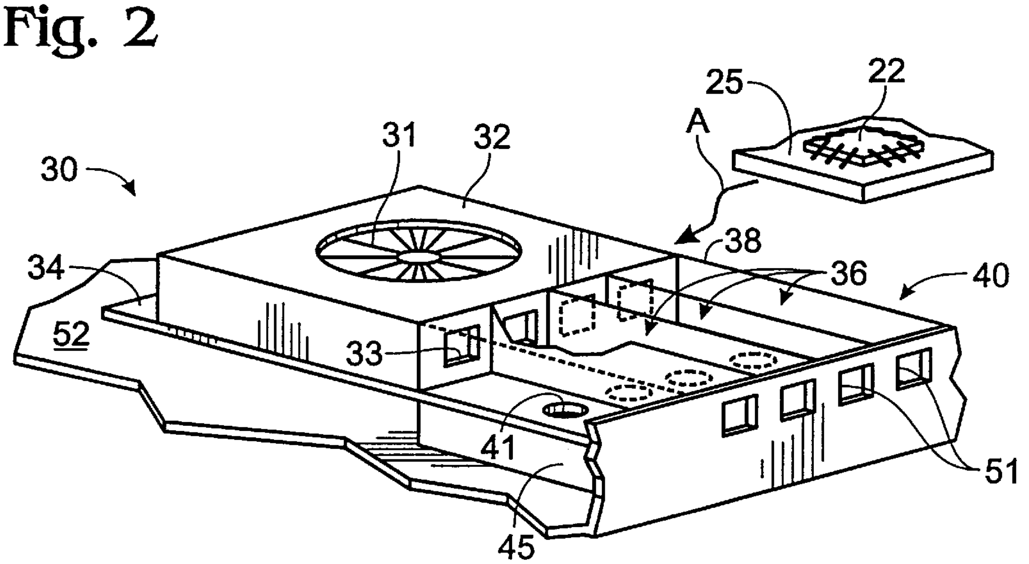
FIG. 2 is a partial perspective view of an electronic device cooling system in accordance with the present invention.

Referring to FIG. 2, a partial perspective view of an electronic device cooling system in accordance with the present invention is shown. Cooling system 30 preferably includes a cooling mechanism 32 and a noise suppression mechanism or structure 40 (hereinafter referred to as open "noise reduction mechanism 40") that suppresses or reduces noise created by the cooling mechanism preferably by acoustic filtering. In a preferred embodiment, the cooling mechanism is an electric fan of the type known in the art for cooling electronic devices and components therein. As such, cooling mechanism 32 is also referred to herein as fan 32 (though the cooling mechanism may be other than a fan without deviating from the present invention).

Fan 32 is preferably coupled to a heat sink 34. A circuit board 25 with a heat producing integrated circuit such as processing circuitry 22 is positioned proximate heat sink 34. Arrow A indicates that the circuit board and processing logic are preferably positioned underneath the heat sink (from the perspective of FIG. 2). Heat sink 34 is preferably formed of an inexpensive, lightweight material that has good thermal conductive properties. Die cast aluminum is an example of such a material.

Figure 4:
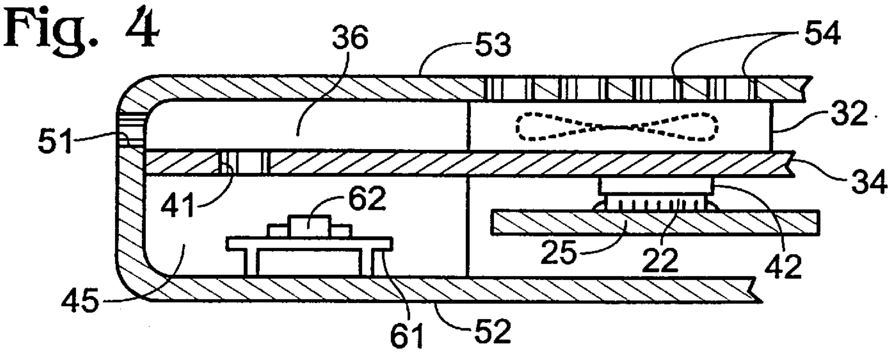
FIG. 4 is a side view of the cooling system and other componentry of FIG. 2 in accordance with the present invention.

Fan 32 has an input 31 and a plurality of output openings 33 which are coupled via ducts to exhaust openings 51. The ducts 36 are preferably separated by dividers 38 and their top surface (not shown in FIG. 2) may be provided by the housing of electronic device 10 as shown in FIG. 4. While dividers and a plurality of openings 51 are shown, it should be recognized that a singular duct and opening 51 or other arrangements could be provided.

Figure 6:
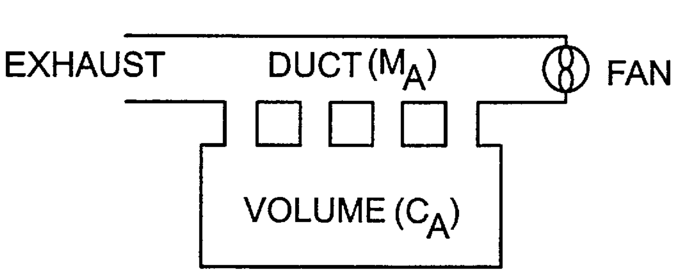
FIG. 6 is a diagram illustrating the parameters $M_A$ and $C_A$ for the embodiment of FIGS. 2 and 4 in accordance with the present invention.

An attenuation orifice 41 is provided in each duct for the purpose of connecting the duct to a compressible air chamber or volume 45 (shown in FIGS. 4 and 6). The arrangement of the attenuation orifice and compressible air chamber serves to dissipate or attenuate noise at undesirable frequencies. Suitable dimensions for the ducts and the compressible air chamber to achieve a desired noise suppression are discussed below.

Figure 3:
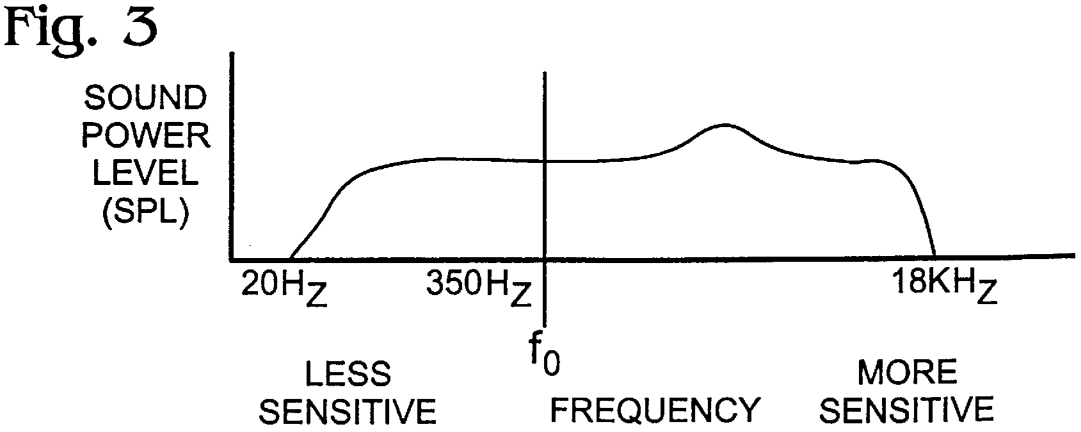
FIG. 3 is a graph of sound power level (SPL) versus frequency.

Referring to FIG. 3, a graph of sound power level (SPL) versus frequency is shown. Studies of the human ear have shown that the range of human hearing is approximately from 20 Hz to 18 KHz. Studies have further shown that humans are less sensitive to frequencies from 20 to 350 Hz than from 350 Hz to 18 KHz. Thus, if a low pass acoustic filter can be established for the fan or other cooling mechanism of an electronic device, than that device will produce significantly less objectionable noise.

Equations related to designing for noise suppression include the following. Equation no. 1 indicates that the cutoff frequency of such a low pass filter is inversely proportional to the square root of $M_A$ times $C_A$, where $M_A$ is the acoustic mass and $C_A$ is the acoustic compliance as defined by Leo L. Beranek in his book entitled "Acoustics" published by the Acoustic Society of America (1954,1993). The American Institute of Physics has accepted Beranek's work as a standard in the acoustics field. Equation no. 1 provides:

$$f_0=1/(\mathbf{90}\ (M_A C_A)^{1/2}) \quad \text{Eq. 1}$$

where $$M_A=(\rho_0 1)/(\pi a^2); \quad \text{Eq. 2}$$

$$C_A=V/(\rho_0 C^2); \quad \text{Eq. 3}$$

and $$1=1'+2(0.85a). \quad \text{Eq. 4}$$

In these equations, $\rho_0$ and C are physical constants having the following values:

$$\rho_0=1.18 \text{ Kg/m3 (density of air)}; \quad \text{Eq. 5}$$

and $$C=345{,}000 \text{ mm/s (speed of sound)}. \quad \text{Eq. 6}$$

The design parameters of cooling system 30 (i.e. for noise suppression mechanism 40) include 1'=length of the exhaust ducts, 1=effective length of duct corrected for air loading of flanged opening, a=equivalent radius of the exhaust ducts (a cross-sectional area indicator) and V=volume of the compressible air chamber.

Combining equations 1–6 provides that the cutoff frequency, $f_0$, is equal to $$194645\ (a/(1'V)^{1/2}. \quad \text{Eq. 7}$$

Assuming that the four ducts 36 of the embodiment of FIGS. 2 and 4 have a cross-sectional area of 100 $mm^2$, then the equivalent radius for this area if it were circular is $r=(\pi\cdot 100)^{1/2}$ or 5.6 mm. The length of the ducts may be established at 25 mm, thus causing 1' to have a value of 25 mm. If the desired cutoff frequency is set at 316 Hz (e.g., below a 350 Hz limit), then substituting the values of a and 1' into Eq. 6 provides a compressible air chamber volume of $4\times10^5$ mm. This volume may be achieved, for example, in a chamber that is 10 mm×200 mm×200 mm and a great number of other configurations, including those that are not uniformly dimensioned. Implementation of such a volume in the cooling system discussed with reference to FIG. 2 is now presented.

Referring to FIG. 4, a side view of the cooling system and other componentry of FIG. 2 in accordance with the present invention is shown. Fan 32 is provided on or proximate a heat sink 34 and processing circuitry 22 is coupled by a thermal joiner 42 to heat sink 34. Thermal joiner 42 is provided for efficient conduction of heat away from processing circuitry 22 to the heat sink. A plurality of inlet openings 54 are provided in housing cover 53 (not shown in FIG. 2) that is coupled to or formed integrally with the remainder of the housing 52. One of the attenuation orifices 41 is shown connecting a duct 36 to the compressible air chamber or volume 45. Volume 45 may have the dimensions of 10 mm in height, 200 mm in width and 200 mm in depth (into the page) to achieve a cutoff frequency (in combination with the duct length and cross-sectional area discussed above) of 316 Hz.

While volume 45 of FIG. 4 has generally uniform dimensions, it should be recognized that these uniform dimensions are provided in part because they permit easier mathematical analysis than non-uniform dimensions. Nonetheless, the present invention may be implemented with curved, round, punctuated and other non-uniform shapes. Furthermore, the volume may be established from otherwise unused air space in the electronic device. As such it is possible that the volume may contain components including other circuitry therein. Accordingly, a representative circuit board 61 with a component 62 provided thereon is shown in FIG. 4. It should be recognized that while the equations provided herein are helpful in cooling system design (particularly from a mathematical or theoretical perspective), the ultimate selection of component layout and dimensions is preferably established empirically.

Figure 5:
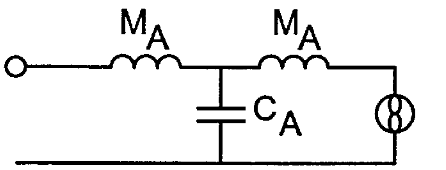
FIG. 5 is an equivalence acoustic circuit diagram for the configuration of FIGS. 2 and 4 in accordance with the present invention.

Referring to FIG. 5, an equivalence acoustic circuit diagram for the configuration of FIGS. 2 and 4 in accordance with the present invention is shown. The term $C_A$ refers to the compressible air space while the $M_A$ terms refers to the duct sections before and after the attenuation orifice(s). This equivalence circuit and others like it can be implemented such that the compressible air chamber is accessed by penetrating the heat sink (as shown in FIG. 4) or such that the compressible air chamber is coupled to the output duct(s) other than through the heat sink, i.e., coupled to the top of the duct(s) or provided around the duct(s) as in FIG. 7 below.

Referring to FIG. 6, a diagram illustrating the parameters $M_A$ and $C_A$ in accordance with the present invention is shown.

Figure 7A:
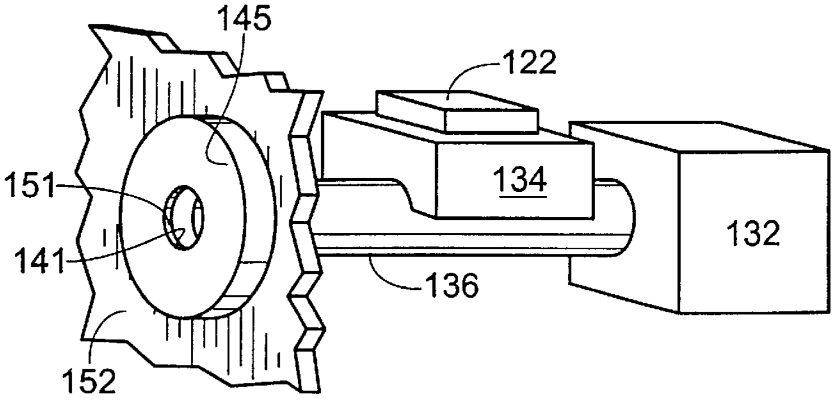
FIG. 7A is a perspective view of an alternative embodiment of a cooling system noise suppression mechanism in accordance with the present invention.

Referring to FIG. 7A, a perspective view of an alternative embodiment of a cooling system noise suppression mechanism in accordance with the present invention is shown. FIG. 7A illustrates one wall of an electronic device housing 152 having a cooling system coupled thereto. Illustrated components include a fan or other cooling mechanism 132, a heat sink 134 and processing logic 122. Processing logic 122, heat sink 134 and fan 132 function in substantially the same manner as components 22, 34 and 32 discussed above. In the cooling system of FIG. 7A, however, the compressible air chamber 145 is configured as a hollow disk or the like that is placed around the fan exhaust duct. Attenuation orifice(s) 141 preferably couples duct 136 to the interior of chamber 145.

Figure 7B:
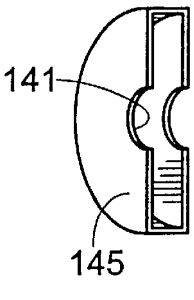
FIG. 7B illustrates a perspective cross-sectional view of the compressible air chamber of FIG. 7A in accordance with the present invention.

FIG. 7B illustrates a perspective cross-sectional view of compressible air chamber 145 in accordance with the present invention.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. An electronic apparatus, comprising:

an electronic data input device;

an electronic data output device;

electronic data processing circuitry coupled between said input device and said output device;

a function performing mechanism associated with said processing circuitry that produces sound waves of audible noise;

an airflow duct that functions as a conduit to provide airflow for said function performing mechanism; and a compressible air chamber coupled to said duct;

wherein said duct and said chamber are configured such that said duct includes a within duct egress orifices that permits sound waves propagating through said duct to be communicated to said chamber, and said chamber defines with the exception of said ingress orifice a substantially closed volume that functions to suppress the sound waves, and wherein at least one divider between said chamber and an adjacent chamber is coupled to a heat sink, said heat sink being coupled to a heat producing integrated circuit.

2. The apparatus of claim 1, wherein said chamber is configured to attenuate sound waves between 350 Hz to 18 KHz.

3. The apparatus of claim 1, wherein said ingress orifice is located in a given portion of said duct and said volume is approximately equal to or less than $(194645 \cdot a/f_0)^2/l'$ $mm^3$, where a is the approximate radius of the given portion of said duct, $f_0$ is an approximate threshold frequency between 350 Hz and 18 KHz and l' is the approximate length of the given portion of said duct.

4. The apparatus of claim 1, wherein said chamber suppresses sound waves above at least approximately 400 Hz.

5. The apparatus of claim 1, wherein the function performing mechanism is a cooling mechanism that cools said electronic data processing circuitry.

6. An electronic device, comprising:

an electronic data input mechanism;

an electronic data output mechanism;

electronic data processing device coupled between said input and output mechanisms;

memory coupled to said processing device;

a cooling mechanism that cools said processing device and has a principal airflow pathway; and a noise reducing mechanism that acoustically filters noise caused by said cooling mechanism, said noise reducing mechanism including a compressible air chamber that is coupled to said pathway about an orifice that permits sound waves from said pathway to be communicated to said compressible air chamber;

said compressible air chamber being further configured with said principal airflow pathway such that said principal airflow pathway does not transverse said compressible air chamber, and wherein at least one divider between said compressible air chamber and an adjacent compressible air chamber is coupled to a heat sink, said heat sink being coupled to a heat producing integrated circuit.

7. The device of claim 6, further comprising supplemental electronic circuitry provided within said compressible air chamber.

8. The apparatus device of claim 6, wherein said substantially closed volume is approximately equal to or less than $(194645 \cdot a/f_0)^2/l'$ $mm^3$, where a is the approximate radius of said pathway, $f_0$ is the approximate threshold frequency of undesired sound waves and l' is the approximate length of said pathway.

9. The device of claim 6, wherein said cooling mechanism includes a fan.

10. The device of claim 6, wherein said noise reducing mechanism provides low pass acoustic filtration.

11. A noise reducing apparatus for reducing noise generated by a function performing mechanism of an electronic device, comprising:

an airflow duct coupled to a function performing mechanism and having a sound wave passage orifice formed therein between an input and output thereof; and a compressible air chamber coupled to said duct about said sound wave passage orifice that performs volumetric acoustic filtering of sound waves generated by said function performing mechanism, said compressible air chamber defining with the exception of said orifice a substantially closed volume and being configured so as to suppress the generated sound waves, and wherein at least one divider between said compressible air chamber and an adjacent compressible air chamber is coupled to a heat sink, said heat sink being coupled to a heat producing integrated circuit.

12. The apparatus of claim 11, wherein said function performing mechanism is a cooling mechanism and said duct is an exhaust duct.

13. The apparatus of claim 11, wherein said generated sound waves include those with frequencies above approximately 400 Hz.

* * * * *

UNITED STATES PATENT AND TRADEMARK OFFICE

CERTIFICATE OF CORRECTION

PATENT NO. : 6,359,989 B2
DATED : March 19, 2002
INVENTOR(S) : Scott N. Hickman et al.

It is certified that error appears in the above-identified patent and that said Letters Patent is hereby corrected as shown below:

Column 5,
Line 32, delete “orifices” and insert therefor -- orifice --

Signed and Sealed this

Twenty-first Day of September, 2004

JON W. DUDAS
*Director of the United States Patent and Trademark Office*